US012672904B2

(12) United States Patent
Simon

(10) Patent No.: US 12,672,904 B2
(45) Date of Patent: Jul. 7, 2026

(54) SPIRAL U-BLADE LAG SCREW

(71) Applicant: Stryker European Operations Limited, Carrigtwohill (IE)

(72) Inventor: Bernd Simon, Kiel (DE)

(73) Assignee: Stryker European Operations Limited, Carrigtwohill (IE)

(*) Notice: Subject to any disclaimer, the term of this patent is extended or adjusted under 35 U.S.C. 154(b) by 44 days.

(21) Appl. No.: 18/436,702

(22) Filed: Feb. 8, 2024

(65) Prior Publication Data

US 2024/0261003 A1      Aug. 8, 2024

Related U.S. Application Data

(60) Provisional application No. 63/444,098, filed on Feb. 8, 2023.

(51) Int. Cl.
*A61B 17/74* (2006.01)
*A61B 17/86* (2006.01)

(52) U.S. Cl.
CPC ........ *A61B 17/744* (2013.01); *A61B 17/8625* (2013.01)

(58) Field of Classification Search
CPC . A61B 17/744; A61B 17/725; A61B 17/8625; A61B 17/8685
See application file for complete search history.

(56) References Cited

U.S. PATENT DOCUMENTS 4,457,301 A * 7/1984 Walker ............... A61B 17/7258
606/62
4,657,001 A    4/1987 Fixel 6,423,066 B1    7/2002 Harder et al.
8,114,078 B2    2/2012 Aschmann
9,642,662 B2    5/2017 Appenzeller et al.
2002/0045900 A1* 4/2002 Harder ................. A61B 17/744
606/65
2006/0084999 A1* 4/2006 Aschmann ........... A61B 17/744
606/64
2007/0123878 A1* 5/2007 Shaver ................... A61B 17/72
606/64

(Continued)

FOREIGN PATENT DOCUMENTS

JP        7154369 B1 * 10/2022    ............. A61B 17/74
WO    WO-2022010062 A1 *  1/2022    ........... A61B 17/725

OTHER PUBLICATIONS

English-language translation of WO 2022010062 A1; accessed on May 20, 2025.*

(Continued)

*Primary Examiner* — Julianna N Harvey
(74) *Attorney, Agent, or Firm* — Lerner David LLP

(57)        ABSTRACT

A lag screw assembly includes a lag screw and a blade. The lag screw includes a shank extending from a proximal end to a distal end along a longitudinal axis, the shank having an outer surface, and the shank having a threaded portion at the distal end. The lag screw further includes a groove formed in the shank and open to the outer surface, the groove extending along the shank between the proximal and distal ends. At least a portion of the groove defines a path that extends around and along the longitudinal axis on the outer surface. The blade has a head and a leg extending therefrom for slidably engaging the groove.

20 Claims, 5 Drawing Sheets

(56)         References Cited

U.S. PATENT DOCUMENTS

| 2010/0063503 A1 * | 3/2010 | Dell'Oca | ............. | A61B 17/744 |
| | | | | 606/62 |
| 2023/0255668 A1 * | 8/2023 | Kim | ....................... | A61B 17/86 |
| | | | | 606/62 |

OTHER PUBLICATIONS

English-language translation of JP 7154369 B1; accessed from EPO on Sep. 5, 2025 (Year: 2022).*

* cited by examiner

X1

SPIRAL U-BLADE LAG SCREW

CROSS-REFERENCE TO RELATED APPLICATIONS

This application claims the benefit of the filing date of U.S. Provisional Patent Application No. 63/444,098 filed on Feb. 8, 2023, the disclosure of which is hereby incorporated herein by reference.

BACKGROUND OF THE INVENTION

It is known in the art to use screws and blades as fastening parts. Screws provide an excellent grip in the axial direction, a moderate grip in the radial direction (perpendicular to the screw axis), and little grip against rotation around the screw axis. Opposing blades provide a very good grip in the radial direction as well as against rotation around the blade axis, but little grip in the axial direction.

One example, as described in U.S. Pat. No. 6,423,066, the disclosure of which is hereby incorporated by reference in its entirety, includes a lag screw adapted to be inserted into the femur through an intramedullary nail, the lag screw defining grooves to receive a U-shaped blade. This solution represents a combination of screws and blades and unites the desired characteristics of both fastening parts. However, loss of reduction of the lag screw and/or rotational failure of the lag screw after hip fracture treatment are potential issues that may arise within a patient over time with a U-blade and lag-screw combination, which may lead to the need for revision surgery.

Thus, further developments are needed to improve fixation performance of the lag screw implanted in the femoral head, particularly in hip fracture treatment procedure

BRIEF SUMMARY OF THE INVENTION

According to a first aspect of the disclosure, a lag screw assembly may include a lag screw including a shank extending from a proximal end to a distal end along a longitudinal axis, the shank having an outer surface, and the shank having a threaded portion at the distal end. The lag screw may further include a groove formed in the shank and open to the outer surface, the groove extending along the shank between the proximal and distal ends. The lag screw assembly may further include a blade having a head and a leg extending therefrom for slidably engaging the groove. At least a portion of the groove may define a path that extends around and along the longitudinal axis on the outer surface.

Further in the lag screw assembly according to the first aspect of the disclosure, the groove may extend along the shank in a helical path. The leg of the blade may be adapted to extend along the shank in the helical path. The groove may extend into the threaded portion of the shank. The head of the blade may be an annular cylindrical portion and the leg may be integral with the annular cylindrical portion. The leg may extend a length greater than a length of the shank. A depth of the groove may vary along a length of the shank. The groove may define a first depth at a threaded portion of the shank and a second depth at a non-threaded portion of the shank, the second depth being greater than the first depth. The groove may define a constant depth at a threaded portion of the shank and a non-threaded portion of the shank. The groove may be separated from the longitudinal axis by a first distance at a threaded portion of the shank and separated from the longitudinal axis by a second distance at a non-threaded portion of the shank, wherein the first distance is greater than the second distance.

Further in the lag screw assembly according to the first aspect of the disclosure, the groove may define a ramp portion between the threaded portion and the non-threaded portion to transition between the first and second depths of the pair of grooves. An end of the leg may have a chamfer on an outer surface thereof. An end of the leg may have a chamfer on an inner surface thereof. The groove may have walls extending inwardly from an open outer surface thereof into the shank, and at the proximal end of the shank, the groove may have a chamfer. The head of the blade may be adapted to be fastened to the proximal end of the shank with a fastener. The fastener may be a screw configured to be threadably coupled to the head of the blade and the proximal end of the shank. The lag screw may include a recess at the proximal end for engaging a tool. The groove may extend from the proximal end of the shank to the distal end of the shank. An outer diameter of the head may substantially correspond in size to an outer diameter of the screw shank. At least a portion of the leg may be adapted to follow the path defined by the groove as the portion of the leg extends along the shank. The blade may be a monolithic component including the head and the leg.

Further in the lag screw assembly according to the first aspect of the disclosure, the groove formed in the shank may be a first groove, and the lag screw may include a second groove formed in the shank and open to the outer surface, the second groove extending along the shank between the proximal end and the distal end. At least a portion of the second groove may define a path that extends simultaneously around and along the longitudinal axis on the outer surface. The first and second grooves may extend into the threaded portion. The first groove and the second groove may diametrically oppose each other along a length of the shank. The leg of the blade may be a first leg, and the blade may include a second leg extending from the head for slidably engaging the second groove. At least a portion of one groove of the pair of grooves may have a depth substantially equal to a thickness of the blade. When the blade is coupled to the shank, a portion of the blade may extend outwardly from at least one of the pair of grooves in the threaded portion a distance greater than a root diameter of a thread of the threaded portion. The head may be cylindrical and define a threaded bore.

A fixation assembly for fixation of a bone may include an intramedullary nail defining a bore therethrough, and the lag screw assembly according to the first aspect of the disclosure. The lag screw assembly may be configured to extend through the bore of the intramedullary nail. The bore defined by the intramedullary nail may be substantially cylindrical and sized to receive the lag screw. The bore defined by the intramedullary nail may be substantially cylindrical and include at least a groove configured to receive the leg of the blade therethrough, wherein the leg is protruding from a circumference of the shank when coupled to the shank. The leg of the blade may be a first leg and the blade may include a second leg forming a pair of legs. The bore defined by the intramedullary nail may be substantially cylindrical and include a pair of opposing grooves configured to receive a corresponding leg of the pair of legs of the blade therethrough. The pair of legs may protrude from a circumference of the shank when coupled to the shank.

According to a second aspect of the disclosure, a method for fixation of a bone may include inserting a lag screw into a head region of a femur, the lag screw comprising a shank having an outer surface and extending along a longitudinal axis from a proximal end to a distal end with a threaded portion included at the distal end, and a groove open to the outer surface extending from the proximal end to the distal end of the shank, the groove defining a path that extends simultaneously around and along the longitudinal axis on the outer surface of the shank, and inserting a leg of a blade extending from a head into the groove such that the leg engages with the groove.

The method according to the second aspect of the disclosure may further include coupling the head of the blade to the proximal end of the shank with a fastener. Inserting the leg may include impacting the head with an impacting tool. The method may further include inserting a nail into an intramedullary canal of the femur, the nail defining a bore configured for insertion of the lag screw therein. The step of inserting the lag screw may include passing the lag screw through the bore of the inserted nail. The bore may define at least one groove, and wherein passing the lag screw through the bore may include passing the leg of the blade through the at least one groove. The groove of the shank may be a first groove, and the shank may include a second groove forming a pair of grooves. The leg of the blade may be a first leg, and the blade may includes a second leg forming a pair of legs. The groove of the bore of the nail may be a first groove, and the bore of the nail may include a second groove forming a pair of grooves. The inserting step may include inserting each of the pair of legs into a corresponding groove of the pair of grooves of the shank and a corresponding groove of the pair of grooves of the bore of the nail.

DETAILED DESCRIPTION

The present disclosure describes a fixation assembly for fixation of a bone. Particularly, the fixation assembly includes a nail and a lag screw assembly configured to engage with the nail. The lag screw assembly includes a lag screw and a blade, the lag screw having a shank and the blade adapted to engage with a groove defined by the shank. The nail is configured to be inserted into a bone, such as the intramedullary canal of a femur, and the lag screw assembly is further configured to be inserted into the bone and passed through a bore defined by the nail to thereby couple the lag screw assembly and the nail. It should be understood that the fracture fixation system described herein may be applied to long bones in general, and while directed to a femur in the present description, it may also be directed to a humerus, tibia and other long bones.

As used herein, the term "proximal," when used in connection with a device or components of a device, refers to the end of the device closer to a user of the device (e.g., surgeon or operator) when the device is being used as intended. On the other hand, the term "distal," when used in connection with a device or components of a device, refers to the end of the device farther away from the user when the device is being used as intended. As used herein, the term "superior" refers to an upward direction on the page or relative to an anatomy of a person standing upright. On the other hand, the term "inferior" refers to a downward direction on the page or relative to an anatomy of a person standing upright. It should be understood that these terms are not limiting, but merely used for ease of description, and that varied orientations may cause directions to differ. As used herein, the terms "substantially," "generally," "approximately" and "about" are intended to mean that slight deviations from absolute are included within the scope of the term so modified.

Figure 1A:
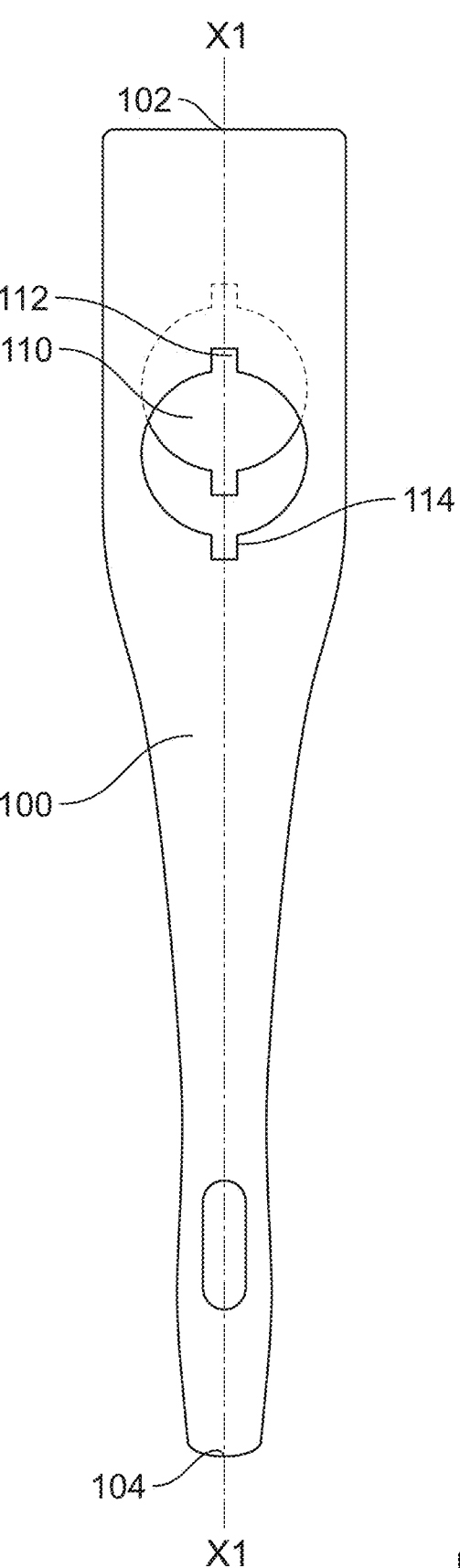
FIGS. 1A-1B are front and perspective views, respectively, of an intramedullary nail according to an embodiment of the disclosure.
Figure 1B:
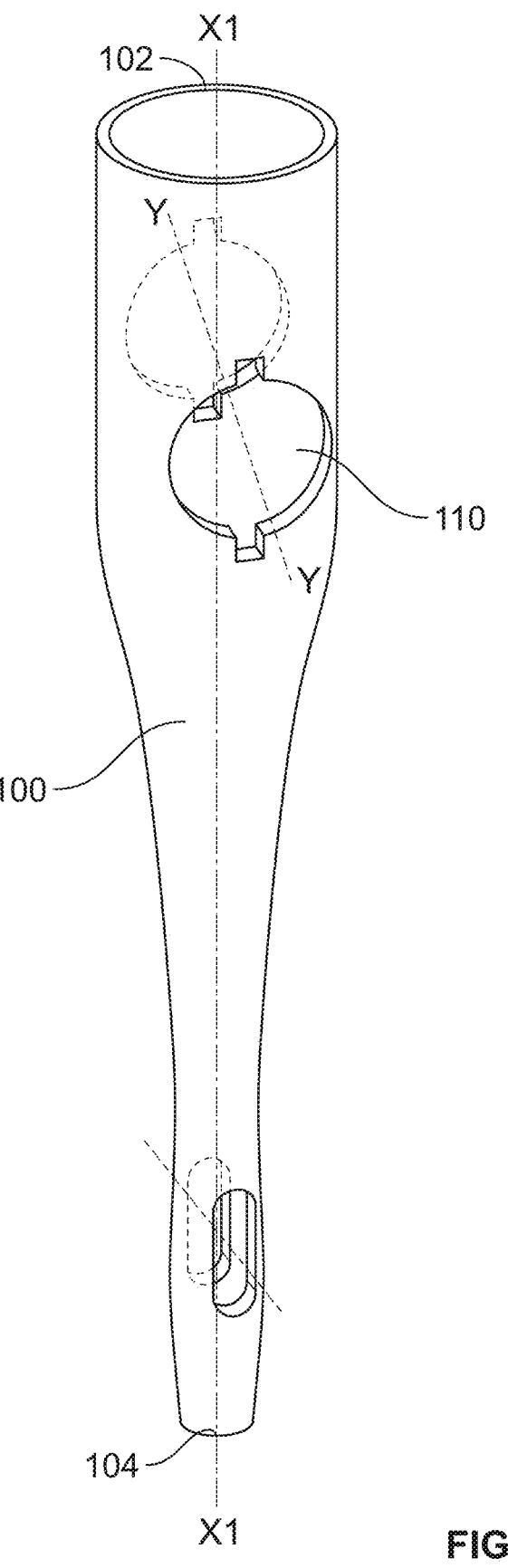

FIG. 1 illustrates an intramedullary nail 100 extending from a proximal end 102 to a distal end 104 along a longitudinal axis X1. The intramedullary nail 100 defines a bore 110 extending generally transversely therethrough along a bore axis Y such that the bore 110 and bore axis Y are aimed along the neck and into the head of a femur when the nail is implanted within the intramedullary canal of the femur. The bore 110 is generally rounded defining a cylindrical shape. In other words, the bore 110 has a generally circular cross-section and extends through an entire thickness of the nail 100 (e.g., through the page in FIG. 1) such that a cylindrical object having a diameter equal to or less than a diameter of the bore 110 may be passed through the bore 110. Bore axis Y intersects and extends at an angle oblique to longitudinal axis X1. It is contemplated that the bore 110 may be defined such that the bore axis Y is orthogonal to the longitudinal axis X1, or such that the bore axis Y forms an acute or obtuse angle with the longitudinal axis X1.

As shown in FIG. 1, the bore 110 includes a first groove 112 and a second groove 114 defined by the intramedullary nail 100 on opposing sides of the bore 110. The first groove 112 is positioned on a proximal or superior side of the bore 110 and the second groove 114 is positioned on a distal or inferior side of the bore 110. That is, the first groove 112 and the second groove 114 extend radially outward from a circumference defined by a cross-section of the bore 110, and similar to the bore 110, the grooves extend through an entire thickness of the nail 100 from one side of the nail 100 to the other. The first and second grooves 112, 114 are slots and are generally rectangularly shaped, e.g., adapted to allow a rectangular shape to pass therethrough.

It is contemplated that the bore 110 of the nail 100 may define any number of grooves. For example, the bore may include only one of the first or second grooves shown in FIG. 1, or the bore may include three, four or more grooves. The grooves may or may not be equally spaced from one another, and may be positioned anywhere along the circumference of the bore. In some examples, the grooves may be angled or arced such that rather than extending straight through the thickness of the nail 100, the grooves extend at least partially along the cross-sectional circumference of the bore as the grooves extend through the thickness of the nail. As bore 110 extends along axis Y, grooves 112, 114 also extend along axis Y so they can interact with a component inserted within bore 110, as described below.

Figure 2:
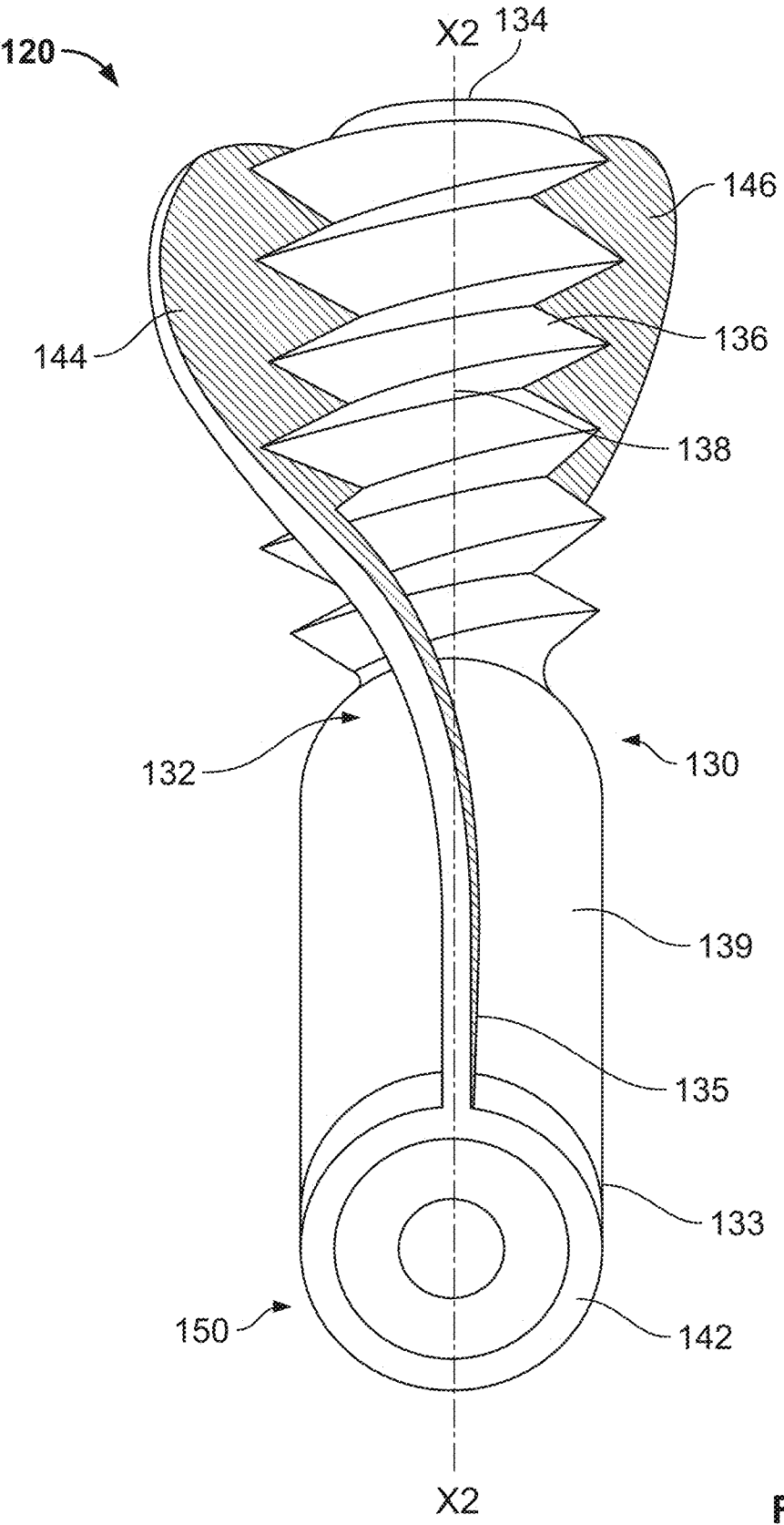
FIG. 2 is a front view of a lag screw assembly according to an embodiment of the disclosure.

FIG. 2 illustrates a lag screw assembly 120 including a lag screw 130 and a blade 150. The lag screw 130 includes a shank 132 extending from a proximal end 133 to a distal end 134 along a longitudinal axis X2. The shank 132 has a threaded portion 138 adjacent the distal end 134 and a non-threaded portion 139 adjacent the proximal end 133. The shank 132 defines two grooves or indentations which extend along a length of the shank 132 and diametrically oppose each other along the length, including a first groove 135 and a second groove 136. The first and second grooves 135, 136 are formed in the shank 132 and open to the outer surface of the shank 132. The grooves 135, 136 each define a path that extends around and along (e.g., parallel to) the longitudinal axis X2 of the shank 132 on the outer surface in a helical or spiral path. Specifically, the proximal portion of each groove 135, 136 in the non-threaded portion 139 of the shank 132 extends along the length of the shank 132 generally parallel to the longitudinal axis X2, and the distal portion of each groove 135, 136 in the threaded portion 138 of the shank 132 both revolves around and extends along the longitudinal axis X2 such that the distal portion of each groove 135, 136 extends helically around the longitudinal axis X2. It is noted that in some embodiments, the grooves of the shank may extend helically around the longitudinal axis for the entire length of the grooves, but that is not necessary to achieve the function of the device, as described in further detail below.

As shown in FIG. 2, the grooves 135, 136 are sized and shaped to receive respective legs of the blade 150. The blade 150 is shown isolated in FIG. 3 and includes a head 142 at the proximal end of the blade 150 along with a first leg 144 and a second leg 146 forming a pair of opposing legs extending distally from the head 142. The legs 144, 146 may be integrally or monolithically formed with the head 142. The first and second legs 144, 146 are sized and shaped to be received by and slidingly engage the first and second grooves 135, 136 of the shaft 132, respectively, and to extend along the helical path of the grooves 135, 136 when the blade 140 is positioned on the shank 132. In the illustrated example, the distal portion of each leg (e.g., the portion forming the helical shape) is shaped to follow the helical path defined by the grooves 135, 136 of the shank 132. That is, the distal portion of each leg is generally helical and arcuate about the longitudinal axis X2, and the proximal portion of each leg is generally parallel to the longitudinal axis X2 such that the proximal portion extends in about the same direction as the longitudinal axis X2 without revolving (or revolving less) about the axis. In some examples, the proximal portions of the legs may not extend straight along the direction of the longitudinal axis X2 and may be partially helical, but may still be less helical or arcuate than the distal portions of the legs. In further examples, the proximal portions of the legs may be equally as helical or arcuate as the distal portions of the legs such that the legs revolve consistently about the longitudinal axis X2 along their entire lengths. Regardless of the shape of the legs, it is contemplated that the grooves 135, 136 of the lag screw 130 generally correspond to the shapes of the legs so that the legs are received by the grooves. The legs 144, 146 may be elastically flexible to flex slightly while being coupled to the lag screw 130 and sliding along the grooves 135, 136. It is therefore contemplated that the blade 140 may be formed of any type of metal or metal alloy which would permit such a degree of flexibility without permanent alteration. In a preferred embodiment, the legs 144, 146 are shaped such that the blade 140 may be coupled to the lag screw 130 by sliding along the longitudinal axis X2 and into the nail 100, and after being assembled with the nail 100, the lag screw assembly 120 including the lag screw 130 and the blade 140 may be capable of sliding together in the proximal direction within the bore 110 of the nail 100, e.g., about 20 millimeters, without significant rotation.

The legs 144, 146 have a thickness greater than a depth of the grooves 135, 136 such that the legs 144, 146 protrude beyond an outer circumference or surface of the shank 130. Furthermore, the distal portion of each leg has a thickness sufficient to protrude beyond the threads formed in the threaded portion 138 of the shank 132. That is, the distal portion of each of the blade legs 144, 146 extends outward from the corresponding groove 135, 136 in the threaded portion 138 of the shank 132 a distance greater than an outer diameter of the threads in the threaded portion 138. The radially outward protrusion of the legs 144, 146 allows the blade 140 to engage with both the grooves 112, 114 in the bore 110 defined by the nail 100 and also with the adjacent femoral bone when the lag screw assembly 120 is inserted into the femur and the nail 100 for improved anchoring and reduced movement of the lag screw assembly when finally implanted.

In the illustrated example, after the lag screw assembly 120 is passed through the bore 110 of the nail 100, the proximal non-threaded portion 139 of the shank 132 is generally disposed within the bore 110 of the nail 100, and the distal threaded portion 138 of the shank 132 is disposed within the neck and into the head of the femur. In such an example, the lag screw assembly 120 includes the distal portion of the legs 144, 146 corresponding to the distal threaded portion 138 of the shank 132, the distal portion of the legs disposed within the grooves 135, 136 and protruding radially outward from the shank 132 to contact and secure the lag screw assembly 120 within the femur and reduce or prevent undesirable rotational or axial movement of the fractured portions of the femur. Further, the lag screw assembly 120 includes the proximal portions of the legs 144, 146 corresponding to the proximal non-threaded portion 139 of the shank 132, the proximal portions of the legs disposed within the grooves 135, 136 and protruding radially outward from the shank 132 to engage with and extend into the corresponding grooves 112, 114 in the bore 110 of the nail 100, which secures the lag screw assembly 120 to the nail 100 and prevents or limits undesirable relative movement.

As shown in FIG. 2, the head 142 of the blade 140 abuts the proximal end 133 of the shank 132 when the blade 140 is coupled to the shank 132. The head 142 is an annular cylindrical portion having an outer diameter which substantially corresponds to an outer diameter of the shank 132, but may also have a smaller outer diameter than the shank 132. The head 142 is also configured to receive a fixation device 155, such as a screw, which extends through the head 142 of the blade and into a threaded bore defined in the shank 132 of the lag screw 130 to couple the blade 140 to the lag screw 130. The head 142 defines a bore therethrough, which may be threaded, to receive the fixation device 155. In some examples, the head 142 may define a collar through which a fixation device 155, such as an end cap, may be placed to affix the blade 140 to the lag screw 130.

Figure 3:
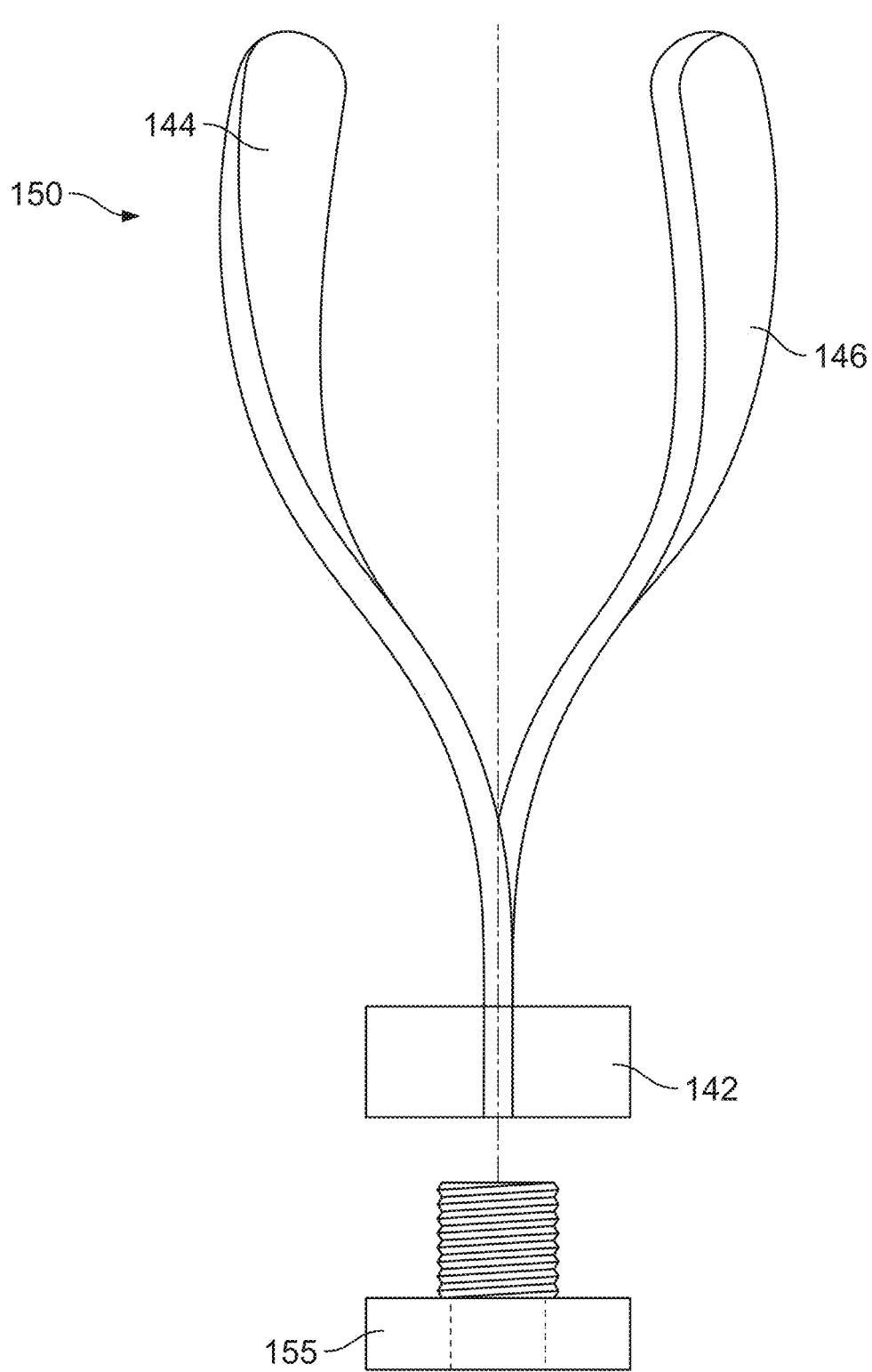
FIG. 3 is an exploded view of a blade and fixation device of the lag screw assembly of FIG. 2.
Figures 4, 5:
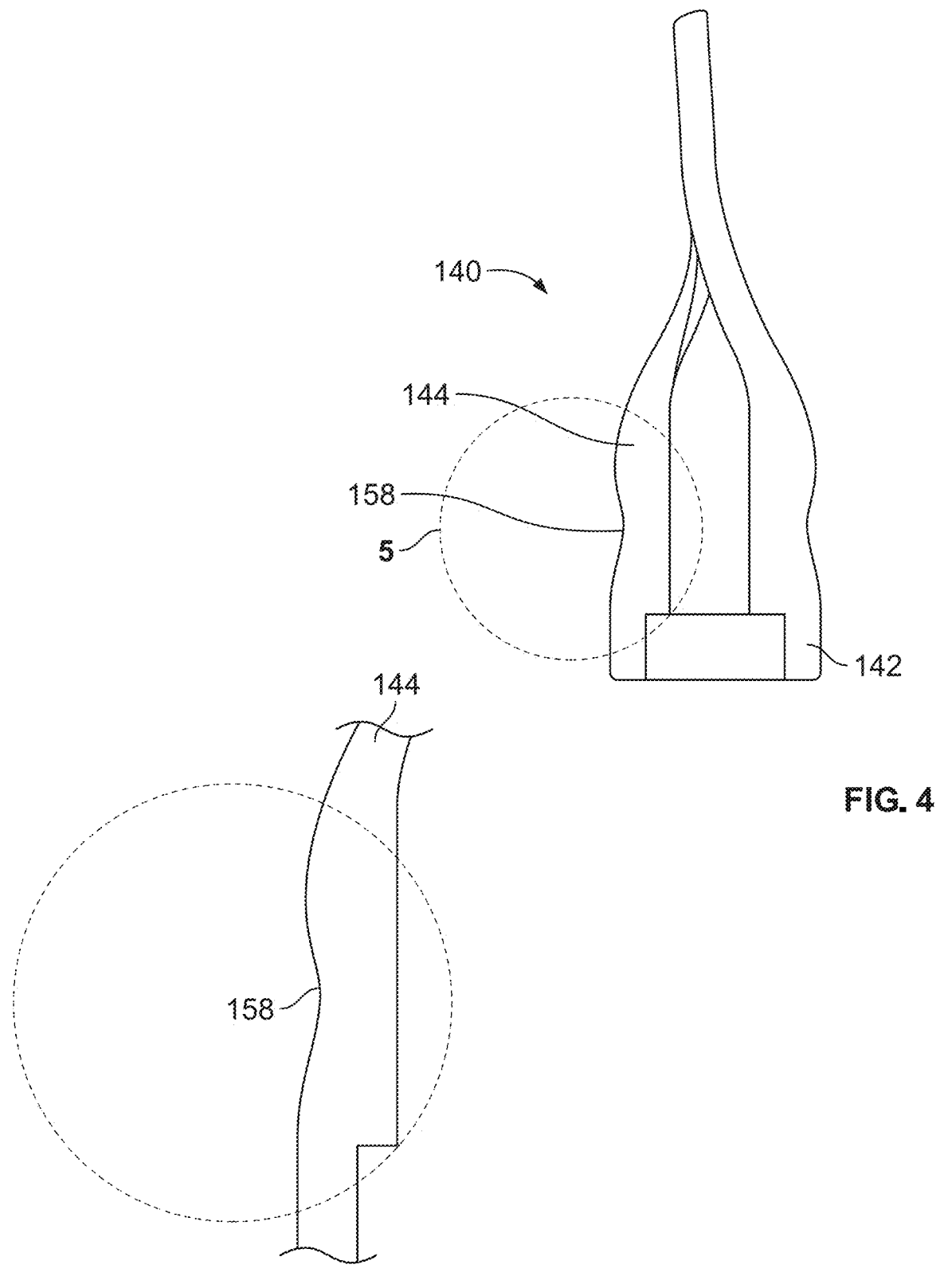
FIG. 4 is a side view of the blade of FIG. 3.
FIG. 5 is a close-up view of a leg of the blade of FIG. 4.

FIG. 4 illustrates a side view of the blade 140, e.g., wherein the blade is rotated approximately 90 degrees relative to the view shown in FIG. 3. A proximal portion of each of the legs 144, 146 of the blade defines an indentation 158, as shown in the close-up view of the first leg 144 in FIG. 5. In some examples, a set screw (not shown) may be included in or applied to the nail 100 to reach the indentation 158 of the first leg 144 such that the distal end of the set screw abuts the indentation of the leg to allow for static locking and limited controlled sliding of the blade 140 relative to the lag screw 130 and/or the nail 100. Such an engagement between the set screw and the blade may prevent the lag screw assembly from sinking further into the femur than desired after the lag screw assembly is fully implanted.

A method for implanting the nail 100 and the lag screw assembly 120 and fixing the bone is described herein. A first bore is formed, e.g., by drilling, reaming, etc., in a proximal or distal end of the femur to form a bore within the intramedullary canal. The nail 100 is then inserted into the intramedullary canal of the femur through the bore in a manner that is well known in the art. Next, a second bore is formed, e.g., by drilling, reaming, etc., in a lateral surface of the femur along the bore axis Y, and the lag screw 130 is then inserted into the femur along the bore axis Y. As the lag screw 130 is inserted into the femur, the lag screw 130 is passed through the bore 110 defined by the nail 100 so that the lag screw 130 extends into the head of the femur.

Thereafter, the blade 150 is advanced such that the legs 144, 146 of the blade 140 surround the lag screw 130. The legs 144, 146 engage with the grooves 135, 136 defined by the lag screw such that the legs 144, 146 slidingly translate along the grooves 135, 136 as the blade 140 is advanced distally over the lag screw 130. The blade 140 is sized such that the distal end of the legs 144, 146 are initially positioned over the proximal end of the shank 132, and the blade is then advanced distally relative to the lag screw 130 until the first and second legs 144, 146 of the blade 140 slide into and along the corresponding grooves 135, 136 defined by the shank. The protruding portions of the legs 144, 146 which extend radially outward beyond the outer circumference of the lag screw 130 engage with and are inserted into the grooves 112, 114 defined by the bore 110 of the nail 100 so as to fix the lag screw assembly 120 relative to the nail 100. The blade 140 may be advanced over and along the shank 132 of the lag screw 130 via impact on the head 142 with an impacting tool, such as a hammer. It is noted that after the lag screw 130 is implanted and before the blade 140 is inserted over the lag screw, the lag screw may be rotationally adjusted so that the grooves 135, 136 on the proximal portion of the lag screw align with the grooves 112, 114 defined by the nail 100. Such alignment allows the legs 144, 146 of the blade 140 to be positioned into corresponding grooves 112, 114 of the nail 100 when the blade 140 is advanced along the shank 132 of the lag screw 130.

After the lag screw 130 and the blade 140 are inserted into the second bore formed in the femur and coupled to one another, the head 142 of the blade 140 is coupled to the proximal end 133 of the shank 132 with the fixation device 155. That is, the fixation device 155 may be screwed through the bore defined by the head 142 of the blade 140 and into the proximal end 133 of the shank 132, which defines a threaded bore adapted to receive and engage with the fixation device 155. The head 142 and/or the proximal end 133 of the shank 132 may include grooves which further facility insertion of the screw 155 therein.

It is contemplated that the shank 132 of the lag screw 130 may define any number of grooves and need not be limited to two grooves. For example, the shank may define only one groove, or may define three or more grooves spaced evenly apart from one another around the circumference of the shank. In such examples, the blade 140 may include a number of legs corresponding to the number of grooves defined in the shank of the lag screw, and the grooves defined in the bore of the nail may further correspond to the number of legs in the blade. The number of grooves may exceed the number of legs, giving flexibility as to how the blade 140 can be positioned with respect to lag screw 130. In other examples, the grooves defined by the shank of the lag screw may not extend the entire length of the lag screw. For instance, the grooves may be only included in the non-threaded portion of the lag screw, or only in the threaded portion of the lag screw, or only partially along each of the threaded and non-threaded portions.

In some examples, the depth of the groove defined in the shank of the lag screw may vary along the length of the shank. For example, the groove may define a first shallower depth along the threaded portion of the shank and a second greater depth along the non-threaded portion of the shank so that the groove is deeper in the non-threaded portion than in the threaded portion. In other examples, the depths may be configured oppositely such that the grooves have a greater depth in the threaded portion than in the non-threaded portion of the shank. In such examples where the depth of the grooves changes along the length of the shank, the varying depths may be connected by a transitioning ramp portion which transitions the groove from the first depth to the second depth.

It is contemplated that the legs of the blade may not protrude beyond the outer circumference of the shank along the entire length of the shank. For instance, at least some portions of the legs may have a thickness which is about equal to or less than the depth of the corresponding portion of the groove in which it is positioned, and therefore such a portion of the leg may not radially protrude from the shank of the lag screw. Each of the grooves defines walls extending radially inward from the open outer surface into the shank, and any portion or all of the groove may have a chamfer between the wall of the groove and the outer perimeter of the shank.

In some examples, the legs of the blade may extend a length greater than a length of the shank of the lag screw such that the legs extend distally beyond the lag screw, deeper into the head of the femur when the assembly is implanted. The distal ends of the legs may define a chamfer on either the inner surface, the outer surface, or both surfaces of the legs.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A lag screw assembly comprising:
   a lag screw including:
      a shank extending from a proximal end to a distal end along a longitudinal axis, the shank having an outer surface, and the shank having a threaded portion at the distal end;
      a groove formed in the shank and open to the outer surface, the groove extending along the shank between the proximal and distal ends,
      wherein at least a portion of the groove defines a path that extends around and along the longitudinal axis on the outer surface; and
   a blade having a head and a leg extending therefrom for slidably engaging the groove, at least a portion of the leg protruding farther in a radial direction than an outer diameter of the threaded portion,
   wherein an outer surface of the leg defines an indentation.

2. The lag screw assembly of claim 1, wherein the groove extends along the shank in a helical path.

3. The lag screw assembly of claim 2, wherein the leg of the blade is adapted to extend along the shank in the helical path.

4. The lag screw assembly of claim 1, wherein the groove extends into the threaded portion of the shank.

5. The lag screw assembly of claim 1, wherein the head of the blade is an annular cylindrical portion and the leg is integral with the annular cylindrical portion, and wherein the head of the blade is adapted to be fastened to the proximal end of the shank with a fastener.

6. The lag screw assembly of claim 5, further comprising a screw configured to be threadably coupled to the head of the blade and the proximal end of the shank.

7. The lag screw assembly of claim 1, wherein a depth of the groove varies along a length of the shank.

8. The lag screw assembly of claim 7, wherein the groove defines a first depth at the threaded portion of the shank and a second depth at a non-threaded portion of the shank, the second depth being greater than the first depth.

9. The lag screw assembly of claim 1, wherein the lag screw includes a recess at the proximal end for engaging a tool.

10. The lag screw assembly of claim 1, wherein the groove extends from the proximal end of the shank to the distal end of the shank.

11. The lag screw assembly of claim 1, wherein an outer diameter of the head substantially corresponds in size to an outer diameter of the screw shank.

12. The lag screw assembly of claim 1, wherein at least a portion of the leg is adapted to follow the path defined by the groove as the portion of the leg extends along the shank.

13. The lag screw assembly of claim 1, wherein the groove formed in the shank is a first groove, and the lag screw includes a second groove formed in the shank and open to the outer surface, the second groove extending along the shank between the proximal end and the distal end.

14. The assembly of claim 13, wherein at least a portion of one of the first groove and the second groove has a depth substantially equal to a thickness of the blade.

15. The assembly of claim 13, wherein the first and second grooves extend into the threaded portion, and wherein when the blade is coupled to the shank, a portion of the blade corresponding to the threaded portion extends outwardly from at least one of the first and second grooves in the threaded portion a distance greater than a root diameter of a thread of the threaded portion.

16. The assembly of claim 1, wherein a first portion of the leg protrudes farther from the groove in the radial direction than a second portion of the leg.

17. A fixation assembly for fixation of a bone, comprising:
an intramedullary nail defining a bore therethrough; and the lag screw assembly of claim 1 configured to extend through the bore of the intramedullary nail.

18. The assembly of claim 17, wherein the bore defined by the intramedullary nail is substantially cylindrical, sized to receive the lag screw, and includes at least a groove configured to receive the leg of the blade therethrough, wherein the leg is protruding from a circumference of the shank when coupled to the shank.

19. A lag screw assembly comprising:
a lag screw including:
a shank extending from a proximal end to a distal end along a longitudinal axis, the shank having an outer surface, and the shank having a threaded portion at the distal end;
a groove formed in the shank and open to the outer surface, the groove extending along the shank between the proximal and distal ends,
wherein at least a portion of the groove defines a helical path on the outer surface; and
a blade having a head and a leg extending therefrom for slidably engaging the groove,
wherein at least a portion of the leg positioned within a portion of the groove defined in the threaded portion protrudes radially beyond an outer diameter of the threaded portion,
wherein an outer surface of the leg defines an indentation.

20. A kit for fixation of a bone, comprising:
a lag screw including:
a shank extending from a proximal end to a distal end along a longitudinal axis, the shank having an outer surface, and the shank having a threaded portion at the distal end;
a groove formed in the shank and open to the outer surface, the groove extending along the shank between the proximal and distal ends,
wherein at least a portion of the groove defines a helical path on the outer surface; and
a blade having a head and a leg extending therefrom for slidably engaging the groove,
wherein at least a portion of the blade corresponding to the threaded portion of the shank protrudes radially beyond an outer diameter of the threaded portion, and
wherein an outer surface of the leg defines an indentation.

* * * * *